United States Patent [19]

Takeuchi et al.

[11] Patent Number: 5,300,721
[45] Date of Patent: Apr. 5, 1994

[54] METHOD FOR SEPARATING 2,6-DIETHYLNAPHTHALENE

[75] Inventors: Genki Takeuchi; Kazuyoshi Kariu; Mitsuru Shiroshita, all of Kitakyushu, Japan

[73] Assignee: Nippon Steel Chemical Co., Ltd., Tokyo, Japan

[21] Appl. No.: 941,177

[22] Filed: Sep. 4, 1992

[30] Foreign Application Priority Data

Aug. 27, 1990 [JP] Japan ............... 2-222574

[51] Int. Cl.$^5$ ............... C07C 2/64; C07C 7/00; C07C 7/12
[52] U.S. Cl. ............... 585/451; 585/804; 585/828; 585/831
[58] Field of Search ............... 585/828, 831, 804, 451

[56] References Cited

U.S. PATENT DOCUMENTS 3,668,267 6/1972 Hedge ............... 585/831

FOREIGN PATENT DOCUMENTS 51-6953 1/1976 Japan .
63-243040 10/1988 Japan .
63-243044 10/1988 Japan .
63-204826 9/1991 Japan .

*Primary Examiner*—Anthony McFarlane
*Assistant Examiner*—Nhat D. Phan
*Attorney, Agent, or Firm*—Birch, Stewart Kolasch & Birch

[57] ABSTRACT

This invention provides a method for separating 2,6-diethylnaphthalene from a mixture of diethylnaphthalene isomers by contacting said mixture with zeolite producing the same powder X-ray diffraction pattern as faujasite and the method can efficiently separate 2,6-diethylnaphthalene from ethylation reaction products containing diethylnaphthalene isomers.

6 Claims, No Drawings

METHOD FOR SEPARATING 2,6-DIETHYLNAPHTHALENE

FIELD OF THE INVENTION AND RELATED ART STATEMENT

This invention relates to a method for separating 2,6-diethylnaphthalene from a mixture of diethylnaphthalene isomers.

2,6-Diethylnaphthalene is a substance useful as an intermediate for 2,6-naphthalenedicarboxylic acid which is in turn useful as an intermediate for polymers.

The ethylation of naphthalene intended for the preparation of 2,6-diethylnaphthalene gives products containing several tens of compounds. In consequence, there has been a strong demand for the establishment of a technique for separating 2,6-diethylnaphthalene from the ethylation reaction products.

It is, however, virtually impossible to isolate 2,6-diethylnaphthalene by distillation as the separation of 2,6-diethylnaphthalene and 2,7-diethylnaphthalene is extremely difficult even by precise fractionation. There is a description in Japan Kokai Tokkyo Koho No. 51-6,953 (1976) of an application of cooling crystallization to the separation of 2,6-diethylnaphthalene from a mixture of diethylnaphthalene isomers. In that method, lowering of the cooling temperature in an attempt to improve the recovery of 2,6-diethylnaphthalene causes 2,7-diethylnaphthalene to separate, but the process is handicapped by low efficiency as its working temperature is limited to an extremely narrow range for the separation of only 2,6-diethylnaphthalene.

The use of zeolite adsorbents is described in Japan Kokai Tokkyo Koho No. 63-243,044 (1988) for the separation of 2,6-dimethylnaphthalene from a mixture of isomers. The use of zeolite adsorbents is also described in Japan Kokai Tokkyo Koho No. 63-243,040 (1988) for the separation of 2,6-diisopropylnaphthalene. The feasibility of separation by adsorption, however, depends on such factors as molecular size and structure and varies from compound to compound. Hence, the processes in Japan Kokai Tokkyo Koho Nos. 63-243,944 (1988) and 63-243,040 (1988) do not teach one the separation of 2,6-diethylnaphthalene.

OBJECT AND SUMMARY OF THE INVENTION

The present inventors have conducted studies to establish an efficient method for separating 2,6-diethylnaphthalene from the ethylation reaction products containing diethylnaphthalene isomers, found that the separation of 2,6-diethylnaphthalene is feasible by contacting a mixture mainly consisting of diethylnaphthalene isomers and distilled from the ethylation reaction products with a zeolite producing which produces the same powder X-ray diffraction pattern as faujasite, Accordingly, it is an object of this invention to provide an efficient method for separating 2,6-diethylnaphthalene from the ethylation reaction products.

Thus, in the separation of 2,6-diethylnaphthalene from a mixture of diethylnaphthalene isomers, this invention relates to a method for separating 2,6-diethylnaphthalene which comprises contacting said mixture containing diethylnaphthalene isomers with a zeolite which produces the same powder X-ray diffraction pattern as faujasite.

The mixture containing diethylnaphthalene isomers useful for this invention, desirably containing predominantly diethylnaphthalenes, is obtained by the simple or fractional distillation of the products from the alkylation or transalkylation of naphthalene with ethylene, ethanol, an ethyl halide, or polyethylbenzenes in the presence of a Friedel-Crafts catalyst such as $AlCl_3$, silica-alumina, zeolites, solid phosphoric acid, and ion exchange resins. As the reaction reaches or approaches the thermodynamic equilibrium, two of the diethylnaphthalene isomers become predominant, namely 2,6-diethylnaphthalene and 2,7-diethylnaphthalene.

The adsorbents to be used for the separation in this invention are zeolites producing the same powder X-ray diffraction pattern as faujasite, namely H faujasite-type zeolites or metal-modified faujasite-type zeolites. Zeolites of this type are commercially available as zeolite X or zeolite Y.

The modifying metals include alkali metals such as lithium, sodium, potassium, and rubidium, alkaline earth metals such as magnesium, calcium, strontium, and barium, Group VIII transition metals such as iron, cobalt, and nickel, Group Ib transition metals such as copper and silver, and Group IIb transition metals such as zinc and two or more kinds of metals may be used for modification. Preferable among the aforesaid metals are lithium, sodium, potassium, calcium, magnesium, barium, silver, nickel, copper, and zinc and more preferable are lithium, sodium, potassium, barium, silver, and copper. Most preferable are faujasite-type zeolites exchanged with one or more kinds of cations selected from lithium, barium, potassium, and sodium, particularly barium- and/or potassium-exchanged Y zeolites.

The modification of faujasite-type zeolites with metals may be effected, for example, by adding metals during the hydrothermal synthesis of zeolites, by depositing a metal on zeolite supports by impregnating zeolites with an aqueous solution of a given metal salt followed by solvent removal, or ion-exchanging zeolites in a solution of a given metal salt under heat. The ion exchange process is desirable as it is less likely to plug the pores than the process for depositing metals on zeolite supports and it does not affect the structure of zeolites themselves.

The quantity of modifying metals on H faujasite-type zeolites, expressed as the number of a modifying metal multiplied by its valence, is preferably 10 to 200%, more preferably 50 to 150%, of the number of Al atoms in said faujasite-type zeolites. Where the modification with a metal is effected by ion exchange in excess of 100%, the metal in question exists as ion and also as metal of zero valence or as oxide. The presence of metal partly in such nonionic state does not exert ill effects.

The faujasite-type zeolites to be used in this invention have a silica to alumina ratio (mol) of 2 or more. This ratio is usually in the range from 2 to 10 in commercially available materials and it can be raised still further by dealumination without harmful effects.

The adsorbents may be dried sufficiently or allowed to absorb some moisture before use in this invention. Adsorbents having some moisture may sometimes show a higher adsorptive capability than those sufficiently dried. In order to control the moisture content, it is convenient to dry the adsorbent sufficiently on the one hand, to add a given amount of moisture to an adsorbate solution on the other, and let the adsorbent absorb the moisture as a result. It is desirable to let the adsorbent absorb 0.5 to 10% by weight of moisture.

It is allowable to use a diluent which does not interfere with the adsorption of adsorbates in the adsorption step of this invention. Preferable as such diluent are paraffins having 5 to 12 carbon atoms which can be separated easily from diethylnaphthalenes and do not interfere with the adsorption of diethylnaphthalenes by zeolites, for example, n-heptane and isooctane.

It is desirable to use a desorbent in the desorption step. Preferable as such desorbents are one compound or a mixture of two or more compounds selected from alkylbenzenes having about 7 to 10 carbon atoms which can be separated easily from diethylnaphthalenes and show good desorptive capability Examples of useful desorbents are toluene, o-xylene, m-xylene, p-xylene, 1,2,4-trimethylbenzene, 1,3,5-trimethylbenzene, ethylbenzene, p-ethylmethylbenzene, o-diethylbenzene, m-diethylbenzene, p-diethylbenzene, and cumene. More preferable are one or more compounds selected from toluene, p-xylene, ethylbenzene, and p-diethylbenzene. It is possible to control the desorptive capability of such desorbents by mixing them with a suitable amount of the above-mentioned diluents, namely, paraffins having 5 to 12 carbon atoms such as n-heptane and isooctane.

According to the method of this invention, it is possible to contact an adsorbent with a mixture mainly consisting of diethylnaphthalene isomers to which a desorbent has been added in the adsorption step and thereafter apply said desorbent in the desorption step. The aforesaid desorbents may be used here.

The separation by adsorption of this invention may be carried out either by a batch process or the so-called chromatographic process or by a continuous process known as pseudo-mobile-bed back flow process.

The adsorption temperature is preferably from room temperature to 350° C. When the temperature exceeds 350° C., reactions such as isomerization become no longer negligible even with the metal-modified zeolites.

The adsorption pressure is from atmospheric to 100 kg/cm² G, preferably from atmospheric to 50 kg/cm² G.

When the purity of 2,6-diethylnaphthalene obtained by the method of this invention is not sufficiently high, it can be raised further by recrystallization. Solvents suitable for the recrystallization are alcohols having 1 to 4 carbon atoms and/or paraffins having 6 to 8 carbon atoms, preferably ethanol and isopropanol.

The mixture mainly consisting of diethylnaphthalenes other than 2,6-diethylnaphthalene recovered after the adsorption step of this invention is returned to the reactor for the ethylation of naphthalene where it is subjected simultaneously to ethylation, transethylation, and isomerization for reuse as a feed for 2,6-diethylnaphthalene. The transethylation and the isomerization may be carried out separately from the ethylation.

The method of this invention can efficiently separate 2,6-diethylnaphthalene from a mixture of diethylnaphthalene isomers and has a great commercial significance.

DETAILED DESCRIPTION OF THE PREFERRED EMBODIMENT

The separating capacity of adsorbents was evaluated on the basis of separation factor with reference to a standard substance (hereinafter referred to as Y) as defined below:

$$\text{Separation factor } \alpha_x = \frac{(\text{Concentration of } X/\text{Concentration of } Y)_u}{(\text{Concentration of } X/\text{Concentration of } Y)_a}$$

where the concentration is in % by weight, X and Y designate isomers of diethylnaphthalene, the subscript a in the denominator refers to the adsorbed phase, and the subscript u in the numerator refers to the unadsorbed phase. Hence, when $\alpha$ is greater than unity, X is adsorbed with more difficulty than Y. On the other hand, when $\alpha$ is less than unity, X is adsorbed more easily than Y. Therefore, where 2,7-diethylnaphthalene is chosen as Y and 2,6-diethylnaphthalene as X, diethylnaphthalenes rich in 2,6-diethylnaphthalene may be recovered from the unadsorbed phase if zeolite capable of making $\alpha$ greater than unity is selected. The diethylnaphthalenes rich in the 2,6-isomer thus recovered may be purified further by distillation, if necessary by fractionation, since the close-boiling 2,7-isomer has been reduced in concentration. If other isomers were separated in advance by fractionation, 2,6-diethylnaphthalene could be recovered in high concentration from the unadsorbed phase. This material may be purified by recrystallization and the like as needed.

Ion-exchanged faujasite-type zeolites were prepared as follows. Zeolite and alumina sol as binder were extruded into moldings with a diameter of 1.5 mm, introduced into a 1N aqueous solution of a metal chloride or nitrate, and refluxed at ambient pressure for 4 hours with gentle stirring. As the acidity of the aqueous solution increases with the progress of ion exchange, the pH was controlled at 5 to 6 by adding the hydroxide of the same metal as in the chloride or nitrate in small quantities. The aqueous solution was renewed, the procedure was repeated, the mixture was subjected to solid-liquid separation, and the solid was washed with water, dried at 110° C., and calcined in a stream of air at 500° C. for 8 hours.

All the faujasite-type zeolites to be used in the adsorption experiments were ground to a size in the range from 16 to 48 mesh and also dried by calcining at 500° C. for 3 hours immediately before use.

Three mixtures of diethylnaphthalenes differing in isomer ratio shown in Table 1 were used as feed in the adsorption experiments. The numerical values in Table 1 refer to the ratio by weight.

EXAMPLES 1 AND 2

Into a glass flask fitted with a stirrer were introduced 50 parts by weight of faujasite-type zeolite as adsorbent, 7 parts by weight of Mixture A of diethylnaphthalenes shown in Table 1, and 193 parts by weight of n-heptane and the resulting mixture was stirred at room temperature (20° C.) and ambient pressure to effect adsorption. The mixture was subjected to solid-liquid separation after a given period of stirring. The solid was returned to the glass flask, 200 parts by weight of toluene was added, and the mixture was stirred at room temperature (20° C.) and ambient pressure for 2 hours to effect desorption. The composition by weight of the n-heptane phase and the toluene phase was determined by gas chromatography and the separation factor earlier defined was calculated with reference to 2,7-diethylnaphthalene as standard. The results are shown in Table 2.

EXAMPLES 3 AND 4

Into a glass flask fitted with a stirrer were introduced 25 parts by weight of faujasite-type zeolite as adsorbent, 3 parts by weight of Mixture A of diethylnaphthalenes shown in Table 1, and 97 parts by weight of n-heptane and the resulting mixture was stirred at room temperature (20° C.) and ambient pressure to effect adsorption.

The mixture was subjected to solid-liquid separation after a given period of stirring. The solid was returned to the glass flask, 100 parts by weight of p-diethylbenzene was added, and the mixture was stirred at room temperature (20° C.) and ambient pressure for 2 hours to effect desorption. The composition by weight of the n-heptane phase and the p-diethylbenzene phase was determined by gas chromatography and the separation factor earlier defined was calculated with reference to 2,7-diethylnaphthalene as standard. The results are shown in Table 2.

EXAMPLES 5 AND 6

Into a glass flask fitted with a stirrer were introduced 50 parts by weight of faujasite-type zeolite as adsorbent, 7 parts by weight of Mixture A of diethylnaphthalenes shown in Table 1, and 193 parts by weight of isooctane and the resulting mixture was stirred at 50° C. and ambient pressure to effect adsorption. The mixture was subjected to solid-liquid separation after a given period of stirring. The solid was returned to the glass flask, 200 parts by weight of p-diethylbenzene was added, and the mixture was stirred at 50° C. and ambient pressure for 2 hours to effect desorption. The composition by weight of the isooctane phase and the p-diethylbenzene phase was determined by gas chromatography and the separation factor earlier defined was calculated with reference to 2,7-diethylnaphthalene as standard. The results are shown in Table 2.

EXAMPLE 7

Into a glass cylinder with an inner diameter of 1.5 cm was introduced 100 g. of Ba-modified Y zeolite and the zeolite was moistened with n-heptane. The height of the zeolite layer was 60 cm at this point. Mixture B of diethylnaphthalenes (5 g.) shown in Table 1 was added in pulse and then 400 g. of n-heptane was supplied in 160 minutes. Thereafter, n-heptane was replaced with toluene and 400 g. of toluene was supplied in 160 minutes. The operation was all performed at room temperature. The effluent from the glass cylinder was collected in 40 fractions, each weighing 20 g. The 10th to 20th fractions were combined and stripped of the n-heptane by evaporation to yield 0.6 g. of Solid A, which was completely dissolved in 5 g. of ethanol. The solution was cooled to 0° C. to separate a solid, which was subjected to solid-liquid separation to yield 0.4 g. of Solid B with a melting point of 50.0° to 50.5° C. The analytical results are shown in Table 3, with the numerical values referring to the ratio by weight.

EXAMPLE 8

Thoroughly dried Ba-modified Y zeolite (150 g.) was immersed in a mixture of 5 g. of water and 195 g. of n-heptane overnight. The moistened Ba-modified Y zeolite (100 g.) was introduced into a glass cylinder with an inner diameter of 1.5 cm and further moistened with n-heptane. The filled layer was 60 cm high at this point. Mixture C of diethylnaphthalenes (1 g.) shown in Table 1 was added in pulse and then 1,300 g. of n-heptane was supplied in 520 minutes. Thereafter n-heptane was replaced with toluene and 300 g. of toluene was supplied in 120 minutes. The operation was all performed at room temperature. The effluent from the glass cylinder was collected in 80 fractions, each weighing 20 g. The 67th fraction which is the first fraction containing toluene was stripped of the toluene by evaporation to yield 0.2 g. of Solid C. The analytical results are shown in Table 3.

EXAMPLE 9

Into a glass flask fitted with a stirrer were introduced 25 parts by weight of K-modified Y zeolite as adsorbent, 3 parts by weight of Mixture A of diethylnaphthalenes having the composition shown in Table 1, and 97 parts by weight of a 1:1 (weight) mixture of n-heptane and toluene and the resulting mixture was stirred at room temperature (20° C.) and ambient pressure to effect adsorption. After a given period of time, the mixture was subjected to solid-liquid separation. The solid was returned to the glass flask, 100 parts by weight of a 1:1 (weight) mixture of n-heptane and toluene was added again, and the resulting mixture was stirred at room temperature (20° C.) and ambient pressure for 2 hours to effect desorption. The composition by weight of the adsorbed and desorbed phases was determined by gas chromatography and the separation factor earlier defined was calculated with reference to 2,7-diethylnaphthalene as standard. The results are shown in Table 2.

EXAMPLES 10–14

Into a glass flask fitted with a stirrer were introduced 25 parts by weight of K-modified Y zeolite as adsorbent, 3 parts by weight of a mixture of diethylnaphthalenes having the composition shown in Table 4, and 97 parts by weight of each of the desorbents shown in Table 5 and the resulting mixture was stirred at room temperature (20° C.) and ambient pressure to effect adsorption. After a given period of time, the mixture was subjected to solid-liquid separation. The solid was rinsed with isooctane. The desorption of the adsorbates was effected in a Soxhlet extractor for 3 hours with the use of 130 part of the same desorbent as used in the adsorption. The composition by weight of the adsorbed and desorbed phases was determined by gas chromatography and the separation factor earlier defined was calculated with reference to 2,7-diethylnaphthalene as standard. The results are shown in Table 5.

TABLE 1

| DEN mixture | 1,7- | 2,6- | 2,7- | 1,3- | 1,6- | 2,3- | Others |
|---|---|---|---|---|---|---|---|
| A | 6.3 | 32.7 | 34.6 | 8.8 | 8.1 | 1.2 | 8.3 |
| B | 7.6 | 49.5 | 24.7 | 13.3 | 4.1 | 0.6 | 0.2 |
| C | 0.6 | 50.5 | 24.0 | 20.7 | 3.4 | 0.2 | 0.6 |

*DEN: Diethylnaphthalenes
*2,6-: 2,6-Diethylnaphthalene

TABLE 2

| Ex. No. | Adsorbent | Adsorption time: min. | $\alpha_{D1}$ | $\alpha_{2,6-}$ | $\alpha_{2,7-}$ | $\alpha_{1,3-}$ | $\alpha_{D2}$ | $\alpha_{D3}$ |
|---|---|---|---|---|---|---|---|---|
| 1 | BaY | 30 | 0.21 | 2.56 | 1.00 | 18.95 | 1.27 | 0.55 |
| 2 | NaX | 30 | 0.71 | 2.10 | 1.00 | 2.68 | 1.11 | 0.88 |
| 3 | BaY | 120 | 0.21 | 1.87 | 1.00 | 7.03 | 0.90 | 0.45 |
| 4 | KY | 120 | 11.9 | 32.3 | 1.00 | 161 | 5.73 | 2.09 |
| 5 | HY | 30 | 0.49 | 0.81 | 1.00 | 4.60 | 0.48 | 0.65 |
| 6 | NaY | 15 | 1.43 | 4.81 | 1.00 | 62.3 | — | 1.34 |
| 9 | KY | 120 | 0.60 | 2.08 | 1.00 | 6.88 | 0.69 | 1.25 |

*BaY: Ba-modified Y zeolite
*$\alpha_{2,6}$: Separation factor of 2,6-diethylnapthalene

TABLE 3

|  | 1,7- | 2,6- | 2,7- | 1,3- | 1,6- | 2,3- |
|---|---|---|---|---|---|---|
| Example 7: Solid A | 0.1 | 94.3 | 4.1 | 1.0 | 0.4 | 0.1 |
| Example 7: Solid B | 0.0 | 99.3 | 0.7 | 0.0 | 0.0 | 0.0 |

TABLE 3-continued

| | 1,7- | 2,6- | 2,7- | 1,3- | 1,6- | 2,3- |
|---|---|---|---|---|---|---|
| Example 8: Solid C | 0.1 | 85.4 | 9.5 | 5.0 | 0.0 | 0.0 |

TABLE 4

| | 2,6-DEN | 2,7-DEN | 1,6-DEN | 1,7-DEN | 1,3-DEN | Others |
|---|---|---|---|---|---|---|
| DEN Mixture | 33.8 | 34.4 | 7.8 | 5.3 | 8.0 | 5.1 |

TABLE 5

| Ex. No. | Desorbent | Adsorption time: min. | $\alpha_{2,6\text{-}}$ | $\alpha_{2,7\text{-}}$ | $\alpha_{1,6\text{-}}$ | $\alpha_{1,7\text{-}}$ | $\alpha_{1,3\text{-}}$ | Amount adsorbed (wt. %) |
|---|---|---|---|---|---|---|---|---|
| 10 | Toluene | 120 | 0.21 | 2.56 | 1.00 | 18.95 | 1.27 | 11.2 |
| 11 | p-Xylene | 120 | 0.71 | 2.10 | 1.00 | 2.68 | 1.11 | 23.0 |
| 12 | m-Diethylbenzene | 120 | 0.21 | 1.87 | 1.00 | 7.03 | 0.90 | 12.3 |
| 13 | p-Diethylbenzene | 120 | 11.9 | 32.3 | 1.00 | 161 | 5.73 | 21.5 |
| 14 | Ethylbenzene | 120 | 0.78 | 2.27 | 1.00 | 3.08 | 1.25 | 22.5 |

*Amount adsorbed: Amount adsorbed (wt. %) = $\frac{\text{weight of DEN adsorbed}}{\text{weight of adsorbent}} \times 100$

What is claimed is:

1. A method for separating 2,6-diethylnaphthalene from mixtures of diethylnaphthalene isomers comprising ethylating naphthalene with at least one ethylating agent, selected from the group consisting of ethylene, ethanol, ethyl halides, and polyethylbenzenes, distilling the reaction mixture of said ethylation to obtain a mixture consisting mainly of diethylnaphthalenes, said mixture containing at least 2,6-diethylnaphthalene and 2,7-diethylnaphthalene, contacting said mixture with a zeolite which produces the same powder X-ray diffraction pattern as faujasite, selectively adsorbing at least 2,7-diethylnaphthalene, and recovering diethylnaphthalenes rich in 2,6-diethylnaphthalene from an unadsorbed phase.

2. A process for preparing 2,6-diethylnaphthalene comprising:
   A. ethylating naphthalene with at least one ethylating agent selected from the group consisting of ethylene, ethanol, ethyl halides and polyethylbenzenes, thus forming a reaction mixture;
   B. distilling said reaction mixture to obtain a distillate mixture containing mainly diethylnaphthalene, said mixture containing at least 2,6-diethylnaphthalene and 2,7-diethylnaphthalene;
   C. contacting said distillate mixture with a Y-zeolite adsorbent, which has been ion-exchanged with one or more cations selected from the group consisting of barium, potassium and sodium;
   D. selectively adsorbing at least 2,7-diethylnaphthalene onto said Y-zeolite adsorbent;
   E. separating said Y-zeolite adsorbent from an unadsorbed phase;
   F. desorbing said 2,7-diethylnaphthalene from said Y-zeolite adsorbent by use of one or more desorbent compounds selected from the group consisting of toluene, p-xylene, ethylbenzene, m-diethylbenzene and p-diethylbenzene; and
   G. recovering diethylnaphthalenes rich in 2,6-diethylnaphthalene from said unadsorbed phase.

3. A process for preparing 2,6-diethylnaphthalene according to claim 2 wherein said Y-zeolite is ion-exchanged with barium.

4. A process for preparing 2,6-diethylnaphthalene according to claim 2 wherein said Y-zeolite is ion-exchanged with potassium.

5. The method of claim 2 wherein said contacting step comprises adding said zeolite to said mixture of diethlnaphthalene isomers and stirring.

6. The method of claim 2 wherein said contacting step comprises a pseudo-mobile-bed back flow step.

* * * * *